(12) United States Patent
Schmidt et al.

(10) Patent No.: US 6,348,329 B1
(45) Date of Patent: Feb. 19, 2002

(54) NUCLEIC ACIDS ENCODING RAT CONNECTIVE TISSUE GROWTH FACTOR (CTGF) AND METHODS OF USE

(75) Inventors: Brian Fredrick Schmidt, Half Moon Bay; Margaret Leah Allen, San Francisco, both of CA (US)

(73) Assignee: Fibrogen, Inc., S. San Francisco, CA (US)

( * ) Notice: Subject to any disclaimer, the term of this patent is extended or adjusted under 35 U.S.C. 154(b) by 0 days.

(21) Appl. No.: 09/187,478

(22) Filed: Nov. 6, 1998

(51) Int. Cl.[7] ..................... C07H 21/00; C07K 14/475; C12N 15/18
(52) U.S. Cl. ..................... 435/69.1; 435/69.4; 435/325; 435/252.3; 435/254.11; 435/320.1; 424/198.1; 536/23.5; 530/399
(58) Field of Search ......................... 536/23.5; 435/69.1, 435/69.4, 325, 252.3, 254.11, 320.1; 530/350, 351, 399; 424/198.1

(56) References Cited

U.S. PATENT DOCUMENTS

| | | |
|---|---|---|
| 5,094,941 A | 3/1992 | Hart |
| 5,147,294 A | 9/1992 | Smith et al. |
| 5,408,040 A | 4/1995 | Grotendorst et al. |
| 5,418,135 A | 5/1995 | Pang |

OTHER PUBLICATIONS

Oemar BS et al. Circulation (United States) Feb. 18, 1997, 95 (4) p831–9.*
M. Marra et al.,, Locus AA763369, The WashU–HHMI Mouse EST project, Jan. 27, 1998, Accessed Dec. 12, 2000. (see attached computer printout).*
N.H. Lee et al., Locus AA799836, Rat Genome Project, Apr. 30, 1998, Accessed Dec. 12, 2000. (see attached computer printout).*
M. Marra et al.,, Locus AA221075, The WashU–HHMI Mouse EST project,Feb. 12, 1997, Accessed Dec. 12, 2000. (see attached computer printout).*
M. Marra et al.,, Locus AA163912, The WashU–HHMI Mouse EST project, Feb. 16, 1997, Accessed Dec. 12, 2000. (see attached computer printout).*
Shimokado et al., Cell, 43:277–286, Nov. 1985.
Campochiaro et al., Exp. Eye Res., 49:217–227, 1989.
Matsuoka et al., Proc. Natl. Acad. Sci., 86:4416–4420, Jun. 1989.
Ryseck et al., Cell Growth and Differentiation, 2:225–233, May 1991.

* cited by examiner

Primary Examiner—Lorraine Spector
(74) Attorney, Agent, or Firm—Gray Cary Ware & Freidenrich LLP; Lisa A. Haile

(57) ABSTRACT

The present invention provides rat connective tissue growth factor (CTGF), means for producing CTGF and therapeutic methods for using CTGF or derivatives therof.

9 Claims, 3 Drawing Sheets

DNA and deduced amino acid sequence of rat clone 2-4-7.

(SEQ ID NO:1) GAATTCGGCACGAGGCCAGACCCACTCCAGTCCGACCTCCTCCAGACGGCAGCAGCCCCAGTGGACAACCCCAGGAGCCA 100
CCACCTGGAGCTCCGGACACCAACCTCCCGCCCCGAGACCGAGTCCAGGCTCCGCCTCTGCACCCCGTGCCTCCTCCTGCC 200
GCGCCCCGACCATGCTCGCCTCCGTCGGGGTCCCGTTAGCCTCGCCCTTGGTCGTCCTGCTCCTGTGCACCCGGCCTGCCACCGGCCAGGACTGCAGCGCGCA 300

(SEQ ID NO:2)        M  L  A  S  V  A  G  P  V  S  L  A  L  V  L  L  L  C  T  R  P  A  T  G  Q  D  C  S  A  Q

GTGTCACTGCCCAGCTGAAGCGGGCGCCCTGCCCCGGGCCTGTGAGCCGTGGTCTGATGGACGGCTGTGCCGCGTCTGCCCAAGCAGCTGGGA 400

C  Q  C  A  A  E  A  A  P  R  C  P  A  G  V  S  L  V  L  D  G  C  G  C  C  R  V  C  A  K  Q  L  G

GAACTGTGCACGGAGCGTGATCCTGCGACCACAAGAGTCTCTTCGCGACTTCGGCTCCCCCGCCAACCGCAAGATTGGCGTGTGCACTGCCAAAG 500

E  L  C  T  E  R  D  P  C  D  P  H  K  S  L  F  C  D  F  G  S  P  A  N  R  K  I  G  V  C  T  A  K

ATGGTGCACCCTGTGTCTTCGGTGGCTCCGTGTACCGCAGCGGCGAGTCCTTCCAAAGCAGTGCAAATACCAGTGCACTTGCCTCTGGATGGGCCGTGGG 600

D  G  A  P  C  V  F  G  G  S  V  Y  R  S  G  E  S  F  Q  S  S  C  K  Y  Q  C  T  C  L  D  G  A  V  G

CTGTGTGCCCCTGTGCAGCATGGACGTGCGCCTGCCCAGCCCTGACTGCCCCTTCCCGAGAAGGTCAAGCTGCCCGGGAAATGCTGTCAGGAATGGGTG 700

C  V  P  L  C  S  M  D  V  R  L  P  S  P  D  C  P  F  P  R  R  V  K  L  P  G  K  C  C  Q  E  W  V

TGTGACGAGCCCAAGGACCGCACAGTGGTTGGCCCTGCCCTAGCTGCCTACAGACTGGAAGACACATTTGGCCCTGACCCAACTATGATGCGAGCCAACT 800

C  D  E  P  K  D  R  T  V  V  G  P  A  L  A  A  Y  R  L  E  D  T  F  G  P  D  P  T  M  M  R  A  N

GCCTGGTCCAGACCACAGAGTGGAGCGCCTGTTCTAAGACCTGTGGGATGGCATCTCCACCGGGTTACCAATGACAATACCTTCTGCAGGCTGGAGAA 900

CTGF sequence comparison.

|  |  | rCTGF.PR (SEQ ID NO:2) |
|---|---|---|
|  |  | Hctgf.pr (SEQ ID NO:3) |
|  |  | Mctgf.pr (SEQ ID NO:4) |

| | | | |
|---|---|---|---|
| 1 | M L A S V A G P V S L A L V - L L - L C T R P A T G Q D C S A Q C Q C A A E A A P R C P A G V S L V | rCTGF.PR |
| 1 | M T A A S M G P V V R V A F V L L A L C S R P A T G Q C N D C S A Q C Q C P D E P A P R C P A G V S L V | Hctgf.pr |
| 1 | M L A S V A G P I S L A L V - L L A L C T R P A T G Q D C S A Q C Q C A A E A A P H C P A G V S L V | Mctgf.pr |
| 49 | L D G C G C C R V C A K Q L G E L C T E R D P C D P H K G L F C D F G S P A N R K K I G V C T A K D G | rCTGF.PR |
| 51 | L D G C G C C R V C A K Q L G E L C T E R D P C D P H K G L F C D F G S P A N R K K I G V C T A K D G | Hctgf.pr |
| 50 | L D G C G C C R V C A K Q L G E L C T E R D P C D P H K G S L F C D F G S P A N R K K I G V C T A K D G | Mctgf.pr |
| 99 | A P C V F G G S V Y R S G E S F Q S S C K Y Q C T C L D G A V G C V P L C S M D V R L P S P D C P F | rCTGF.PR |
| 101 | A P C I F G G T V Y R S G E S F Q S S C K Y Q C T C L D G A V G C M P L C S M D V R L P S P D C P F | Hctgf.pr |
| 100 | A P C V F G G S V Y R S G E S F Q S S C K Y Q C T C L D G A V G C V P L C S M D V R L P S P D C P F | Mctgf.pr |
| 149 | P R R V K L P G K C C E E W V C D E P K D R T V V G P A L A A Y R L E D T F G P D P T M M R A N C L | rCTGF.PR |
| 151 | P R R V K L P G K C C E E W V C D E P K D Q T A V G P A L A A Y R L E D T F G P D P T M M I R A N C L | Hctgf.pr |
| 150 | P R R V K L P G K C C E E W V C D E P K D R T A V G P A L A A Y R L E D T F G P D P T M M R A N C L | Mctgf.pr |
| 199 | V Q T T E W S A C S K T C G M G I S T R V T N D N T F C R L E K Q I R L C M V R P C E A D L E E N I | rCTGF.PR |
| 201 | V Q T T E W S A C S K T C G M G I S T R V T N D N A S C R L E K Q S R L C M V R P C E A D L E E N I | Hctgf.pr |
| 200 | V Q T T E W S A C S K T C G M G I S T R V T N D N T F C R L E K Q S R L C M V R P C E A D L E E N I | Mctgf.pr |
| 249 | K K G K K C I R T P K I A K P V K F E L S G C T S V K T Y R A K F C G G V C T D G R C C T P H R T T T | rCTGF.PR |
| 251 | K K G K K C I R T P K I S K P I K F E L S G C T S M K T Y R A K F C G G V C T D G R C C T P H R T T T | Hctgf.pr |
| 250 | K K G K K C I R T P K I A K P V K F E L S G C T S V K T Y R A K F C G G V C T D G R C C T P H R T T T | Mctgf.pr |
| 299 | L P V E F K C P D G E I M K K N M M F I K T C A C H Y N C P G D N D I F P C M Y Y R K M Y G D M A . | rCTGF.PR |
| 301 | L P V E F K C P D G E V M K K N M M F I K T C A C H Y N C P G D N D I F E S L Y Y R K M Y G D M A . | Hctgf.pr |
| 300 | L P V E F K C P D G E I M K K N M M F I K T C A C H Y N C P G D N D I F E S L Y Y R K M Y G D M A . | Mctgf.pr |

Decoration "Decoration #1": Box residues that match the Consensus exactly.

FIG. 2

SEQUENCE LISTING

```
<160> NUMBER OF SEQ ID NOS: 2

<210> SEQ ID NO 1
<211> LENGTH: 2350
<212> TYPE: DNA
<213> ORGANISM: Normal Rate Kidney Fibroblast
<220> FEATURE:
<221> NAME/KEY: CDS
<222> LOCATION: (212)..(1252)

<400> SEQUENCE: 1
gaattcggca cgaggccaga cccactccag ctccgaccct aggagaccga cctcctccag      60
acggcagcag ccccagccca gtggacaacc ccaggagcca ccacctggag cgtccggaca     120
ccaacctccg ccccgagacc gagtccaggc tccggccgcg cccctcgtcg cctctgcacc     180
ccgctgtgcg tcctcctgcc gcgccccgac c atg ctc gcc tcc gtc gcg ggt       232
                                  Met Leu Ala Ser Val Ala Gly
                                   1               5 ccc gtt agc ctc gcc ttg gtg ctc ctc ctc tgc acc cgg cct gcc acc       280
Pro Val Ser Leu Ala Leu Val Leu Leu Leu Cys Thr Arg Pro Ala Thr
        10                  15                  20 ggc cag gac tgc agc gcg cag tgt cag tgc gca gct gaa gcg gcg ccg       328
Gly Gln Asp Cys Ser Ala Gln Cys Gln Cys Ala Ala Glu Ala Ala Pro
    25                  30                  35 cgc tgc ccc gcc ggc gtg agc ctg gtg ctg gac ggc tgc ggc tgc tgc       376
```

```
Arg Cys Pro Ala Gly Val Ser Leu Val Leu Asp Gly Cys Gly Cys Cys
 40                  45                  50                  55 cgc gtc tgc gcc aag cag ctg gga gaa ctg tgc acg gag cgt gat ccc    424
Arg Val Cys Ala Lys Gln Leu Gly Glu Leu Cys Thr Glu Arg Asp Pro
             60                  65                  70 tgc gac cca cac aag agt ctc ttc tgc gac ttc ggc tcc ccc gcc aac    472
Cys Asp Pro His Lys Ser Leu Phe Cys Asp Phe Gly Ser Pro Ala Asn
         75                  80                  85 cgc aag att ggc gtg tgc act gcc aaa gat ggt gca ccc tgt gtc ttc    520
Arg Lys Ile Gly Val Cys Thr Ala Lys Asp Gly Ala Pro Cys Val Phe
         90                  95                 100 ggt ggg tcc gtg tac cgc agc ggc gag tcc ttc caa agc agt tgc aaa    568
Gly Gly Ser Val Tyr Arg Ser Gly Glu Ser Phe Gln Ser Ser Cys Lys
        105                 110                 115 tac cag tgc act tgc ctg gat ggg gcc gtg ggc tgt gtg ccc ctg tgc    616
Tyr Gln Cys Thr Cys Leu Asp Gly Ala Val Gly Cys Val Pro Leu Cys
120                 125                 130                 135 agc atg gac gtg cgc ctg ccc agc cct gac tgc ccc ttc ccg aga agg    664
Ser Met Asp Val Arg Leu Pro Ser Pro Asp Cys Pro Phe Pro Arg Arg
                140                 145                 150 gtc aag ctg ccc ggg aaa tgc tgt cag gaa tgg gtg tgt gac gag ccc    712
Val Lys Leu Pro Gly Lys Cys Cys Gln Glu Trp Val Cys Asp Glu Pro
        155                 160                 165 aag gac cgc aca gtg gtt ggc cct gcc cta gct gcc tac cga ctg gaa    760
Lys Asp Arg Thr Val Val Gly Pro Ala Leu Ala Ala Tyr Arg Leu Glu
        170                 175                 180 gac aca ttt ggc cct gac cca act atg atg cga gcc aac tgc ctg gtc    808
Asp Thr Phe Gly Pro Asp Pro Thr Met Met Arg Ala Asn Cys Leu Val
        185                 190                 195 cag acc aca gag tgg agc gcc tgt tct aag acc tgt ggg atg ggc atc    856
Gln Thr Thr Glu Trp Ser Ala Cys Ser Lys Thr Cys Gly Met Gly Ile
200                 205                 210                 215 tcc acc cgg gtt acc aat gac aat acc ttc tgc agg ctg gag aag cag    904
Ser Thr Arg Val Thr Asn Asp Asn Thr Phe Cys Arg Leu Glu Lys Gln
                220                 225                 230 att cgt ctc tgc atg gtc agg ccc tgt gaa gct gac cta gag gaa aac    952
Ile Arg Leu Cys Met Val Arg Pro Cys Glu Ala Asp Leu Glu Glu Asn
                235                 240                 245 att aag aag ggc aaa aag tgc atc cgg acg cct aaa att gcc aag cct   1000
Ile Lys Lys Gly Lys Lys Cys Ile Arg Thr Pro Lys Ile Ala Lys Pro
        250                 255                 260 gtc aag ttt gag ctt tct ggc tgc acc agt gtg aag acc tac cgg gct   1048
Val Lys Phe Glu Leu Ser Gly Cys Thr Ser Val Lys Thr Tyr Arg Ala
        265                 270                 275 aag ttc tgt ggg gtg tgc acg gac ggc cgc tgc tgc aca ccg cac aga   1096
Lys Phe Cys Gly Val Cys Thr Asp Gly Arg Cys Cys Thr Pro His Arg
280                 285                 290                 295 acc acc aca ctg ccg gtg gag ttc aag tgc ccc gat ggc gag atc atg   1144
Thr Thr Thr Leu Pro Val Glu Phe Lys Cys Pro Asp Gly Glu Ile Met
                300                 305                 310 aaa aag aac atg atg ttc atc aag acc tgt gcc tgc cat tac aac tgt   1192
Lys Lys Asn Met Met Phe Ile Lys Thr Cys Ala Cys His Tyr Asn Cys
                315                 320                 325 ccc ggg gac aat gac atc ttt ccg tgt atg tac tac agg aag atg tat   1240
Pro Gly Asp Asn Asp Ile Phe Pro Cys Met Tyr Tyr Arg Lys Met Tyr
                330                 335                 340 gga gac atg gcg taaagccagg gagtcaggtg acacgaactc atttcagact        1292
Gly Asp Met Ala
        345
```

-continued

```
ataacttgaa ctgagttaca tctcattttc ttctgtaaaa aaacaaaaag gattacagta      1352
gcacattaat ttaaatctgg gttcctaact gctgtgggag aaaacacccc accgaagtga      1412
gaaccgtgtg tcattgtcat gcaaatagcc tgtcaatctc agacactggt ttcgagacag      1472
tttagacttg acagttgttc actagcgcta cagtgacaga acgcacacta aggtgagcct      1532
cctggaaagt ggagatgcc aggagaaaga caggtactag ctgaggtcat tttacaagca      1592
gcgatatgcc tacttttttgg agtgtgacag gggagggaca ttatagcttg cttgcagaca      1652
gacctgctct agcaagagct gggtgtgtgt cctccactcg gtgaggctga agccagctat      1712
tctttcagta agaacagcag tttcagcgct gacattctga ttccagtgac actggtcggg      1772
agtcaggacc ttgtctatta gactggacag cttgtggcaa gtgaatttgc cggtaacaag      1832
ccagattttt atggatgtgg taaatattgt gggtaaatat atatatttgt acagttatct      1892
aagttaattt aaagacgttt gtgcctattg ttcttgtttt aaagtgcttt tggaattttt      1952
aaactgatag cctcaaactc caaacaccat cgataggaca taaagcttgt ctgtgattca      2012
aaacaaagga gatactgcag tggaaactgt aacctgagtg actgtctgtc agaacatatg      2072
gtacgtagac ggtaaagcaa tggatcagaa gtcagatttc tagtaggaaa tgtaaaatca      2132
ctgttggcga acaaatggcc tttattaaga aatggcttgc tcagggtaac tggtcagatt      2192
tccacgagga agtgtttgct gcttctttga ctatgactgg tttgggaggc agtttatttg      2252
ttgagagtgt gaccaaaagt tacatgtttg cacctttcta gttgaaaata aagtatatat      2312 atttttttata tgaaaaaaaa aaaaaaaaaa aactcgag                             2350
```

<210> SEQ ID NO 2
<211> LENGTH: 347
<212> TYPE: PRT
<213> ORGANISM: Normal Rate Kidney Fibroblast

<400> SEQUENCE: 2

```
Met Leu Ala Ser Val Ala Gly Pro Val Ser Leu Ala Leu Val Leu Leu
  1               5                  10                  15

Leu Cys Thr Arg Pro Ala Thr Gly Gln Asp Cys Ser Ala Gln Cys Gln
                 20                  25                  30

Cys Ala Ala Glu Ala Ala Pro Arg Cys Pro Ala Gly Val Ser Leu Val
             35                  40                  45

Leu Asp Gly Cys Gly Cys Cys Arg Val Cys Ala Lys Gln Leu Gly Glu
         50                  55                  60

Leu Cys Thr Glu Arg Asp Pro Cys Asp Pro His Lys Ser Leu Phe Cys
 65                  70                  75                  80

Asp Phe Gly Ser Pro Ala Asn Arg Lys Ile Gly Val Cys Thr Ala Lys
                 85                  90                  95

Asp Gly Ala Pro Cys Val Phe Gly Gly Ser Val Tyr Arg Ser Gly Glu
            100                 105                 110

Ser Phe Gln Ser Ser Cys Lys Tyr Gln Cys Thr Cys Leu Asp Gly Ala
            115                 120                 125

Val Gly Cys Val Pro Leu Cys Ser Met Asp Val Arg Leu Pro Ser Pro
        130                 135                 140

Asp Cys Pro Phe Pro Arg Arg Val Lys Leu Pro Gly Lys Cys Cys Gln
145                 150                 155                 160

Glu Trp Val Cys Asp Glu Pro Lys Asp Arg Thr Val Val Gly Pro Ala
                165                 170                 175

Leu Ala Ala Tyr Arg Leu Glu Asp Thr Phe Gly Pro Asp Pro Thr Met
            180                 185                 190
```

-continued

```
Met Arg Ala Asn Cys Leu Val Gln Thr Thr Glu Trp Ser Ala Cys Ser
        195                 200                 205

Lys Thr Cys Gly Met Gly Ile Ser Thr Arg Val Thr Asn Asp Asn Thr
    210                 215                 220

Phe Cys Arg Leu Glu Lys Gln Ile Arg Leu Cys Met Val Arg Pro Cys
225                 230                 235                 240

Glu Ala Asp Leu Glu Glu Asn Ile Lys Lys Gly Lys Lys Cys Ile Arg
                245                 250                 255

Thr Pro Lys Ile Ala Lys Pro Val Lys Phe Glu Leu Ser Gly Cys Thr
            260             265                 270

Ser Val Lys Thr Tyr Arg Ala Lys Phe Cys Gly Val Cys Thr Asp Gly
        275                 280                 285

Arg Cys Cys Thr Pro His Arg Thr Thr Thr Leu Pro Val Glu Phe Lys
    290                 295                 300

Cys Pro Asp Gly Glu Ile Met Lys Lys Asn Met Met Phe Ile Lys Thr
305                 310                 315                 320

Cys Ala Cys His Tyr Asn Cys Pro Gly Asp Asn Asp Ile Phe Pro Cys
                325                 330                 335

Met Tyr Tyr Arg Lys Met Tyr Gly Asp Met Ala
            340             345
```

NUCLEIC ACIDS ENCODING RAT CONNECTIVE TISSUE GROWTH FACTOR (CTGF) AND METHODS OF USE

FIELD OF THE INVENTION

This invention relates generally to the field of growth factors, more specifically to connective tissue growth factors (CTGF).

BACKGROUND OF THE INVENTION

Growth factors can be broadly defined as multifunctional, locally acting, intercellular signaling polypeptides which control both the ontogeny and maintenance of tissue form and function. The protein products of many of proto-oncogenes have been identified as growth factors and growth factor receptors. Normal versions of many oncogenes first discovered in mammals are also present in the genomes of organisms as disparate as yeast, drosophila, and frogs, and that they function during embryogenesis.

Growth factors stimulate target cells to proliferate, differentiate and organize in developing tissues. The action of growth factors is dependent on their binding to specific receptors which stimulates a signaling event within the cell. Examples of growth factors include platelet-derived growth factor (PDGF), insulin-like growth factor (IGF-I, IGF-II), transforming growth factor beta (TGF-β), transforming growth factor alpha (TGF-α), epidermal growth factor (EGF), acidic and basic fibroblast growth factors (aFGF, bFGF) and connective tissue growth factor (CTGF) which are known to stimulate cells to proliferate.

PDGF is a cationic, heat stable protein found in the alpha granules of circulating platelets and is known to be a mitogen and a chemotactic agent for connective tissue cells such as fibroblasts and smooth muscle cells. Because of the activities of this molecule, PDGF is believed to be a major factor involved in the normal healing of wounds and pathologically contributing to such conditions as atherosclerosis and fibrotic conditions. PDGF is a dimeric molecule consisting of combinations of α and/or β chains. The chains form heterodimers or homodimers and all combinations isolated to date are biologically active.

Studies on the role of various growth factors in tissue regeneration and repair have led to the discovery of PDGF-like proteins. These proteins share both immunological and biological activities with PDGF and can be blocked with antibodies specific to PDGF.

Polypeptide growth factors and cytokines are emerging as an important class of uterine proteins that may form growth signaling pathways between the maternal uterus and developing embryo or fetus. Studies in a variety of species have suggested that EGF, connective tissue EGF-like growth factor (HB-EGF), IGF-I, IGF-II, aFGF, bFGF, pleitrophin (PTN), leukemia inhibitory factor, colony-stimulating factor-1 (CSF-1), and TGF-α may be among the uterine growth-regulatory molecules involved in these processes.

CTGF is a cysteine-rich monomeric peptide of $M_r$ 38,000, which is a growth factor having mitogenic and chemotactic activities for connective tissue cells. CTGF is secreted by cells and is active upon interaction with a specific cell-surface receptor. CTGF is the product of a gene unrelated to the α or β chain genes of PDGF. It is a member of a family of growth regulators which includes the mouse (also know as fisp-12 or βIG-M2) and human CTGF, Cyr61 (mouse), Cef10 (chicken), and Nov (chicken). Based on sequence comparisons, it has been suggested that the members of this family all have a modular structure, consisting of (1) an insulin-like growth factor domain responsible for binding, (2) a von Willebrand factor domain responsible for complex formation, (3) a thrombospondin type I repeat, possibly responsible for binding matrix molecules, and (4) a C-terminal module found in matrix proteins, postulated to be responsible for receptor binding.

The sequence of the cDNA for human CTGF (hCTGF) contains an open reading frame of 1047 nucleotides with an initiation site at position 130 and a TGA termination site at position 1177 and encodes a peptide of 349 amino acids. There is only a 40% sequence homology between the CTGF cDNA and the cDNA for either the α or β chains of PDGF.

The hCTGF open reading flame encodes a polypeptide which contains 39 cysteine residues, indicating a protein with multiple intramolecular disulfide bonds. The amino terminus of the peptide contains a hydrophobic signal sequence indicative of a secreted protein and there are two N-linked glycosylation sites at asparagine residues 28 and 225 in the amino acid sequence. There is a 45% overall sequence homology between the CTGF polypeptide and the polypeptide encoded by the CEF-10 mRNA transcript; the homology reaches 52% when a putative alternative splicing region is deleted.

CTGF is antigenically related to PDGF although there is little if any peptide sequence homology. Anti-PDGF antibody has high affinity to the non-reduced forms of PDGF or CTGF, and ten-fold less affinity to the reduced forms of these peptides, which lack biological activity. This suggests that there are regions of shared tertiary structure between the PDGF isomers and the CTGF molecule, resulting in common antigenic epitopes.

The synthesis and secretion of CTGF are selectively induced by TGF-β, BMP-2 and possibly other members of the TGP-β superfamily of proteins. Although TGP-β can stimulate the growth of normal fibroblasts in soft agar, CTGF alone cannot induce this property in fibroblasts. However, it has been shown that the synthesis and action of CTGF are essential for the TGF-β to stimulate anchorage independent fibroblast growth.

It is probable that CTGF, or fragments thereof, functions as a growth factor in wound healing. Pathologically, CTGF has been postulated to be involved in conditions in which there is an overgrowth of connective tissue cells, such as systemic sclerosis, cancer, fibrotic conditions, and atherosclerosis.

The primary biological activities of CTGF polypeptide is its mitogenicity, or ability to stimulate target cells to proliferate and its role in the synthesis of the extracellular matrix. The ultimate result of this mitogenic activity in vivo, is the growth of targeted tissue. CTGF also possesses chemotactic activity, which is the chemically induced movement of cells as a result of interaction with particular molecules.

SUMMARY OF THE INVENTION

The present invention provides a polynucleotide and a polypeptide encoded thereby which has been identified as rat connective tissue growth factor (CTGF). In accordance with one aspect of the present invention, there is provided a novel recombinant CTGF, as well as active fragments, analogs and derivatives thereof.

In accordance with another aspect of the present invention, there are provided isolated nucleic acid molecules encoding the CTGF of the present invention including mRNA, DNA, cDNA, genomic DNA as well as active analogs and fragments of the protein.

In yet another aspect, the invention provides a method for producing a CTGF polypeptide by recombinant techniques comprising culturing recombinant prokaryotic and/or eukaryotic host cells, containing a nucleic acid sequence encoding a protein of the present invention, under conditions promoting expression of the protein and subsequent recovery of the protein. In a further aspect of the present invention, there are provided antibodies which bind to CTGFs.

In another aspect, the invention provides a polynucleotide for inhibiting expression of CTGF in a cell which comprises a contiguous nucleotide sequence complementary to a CTGF target nucleic acid sequence in a cell, and wherein the polynucleotide hybridizes to the CTGF target nucleic acid sequence thereby inhibiting expression of CTGF as compared to an uninhibited level of CTGF expression in the cell.

The invention further provides a method for inhibiting the expression of CTGF in a cell comprising contacting the cell with a polynucleotide containing a contiguous nucleotide sequence complementary to a CTGF target nucleic acid sequence in a cell, wherein the polynucleotide inhibits the expression of CTGF in the cell.

In accordance with yet a further aspect of the invention, there is provided a method for inhibiting the expression of CTGF in a subject comprising administering a polynucleotide containing a contiguous nucleotide sequence complementary to a CTGF target nucleic acid sequence in a cell to a subject, the polynucleotide is expressed at a level sufficient to inhibit expression of CTGF in the subject.

BRIEF DESCRIPTION OF THE DRAWINGS

The following drawings are illustrative of embodiments of the invention and are not meant to limit the scope of the invention as encompassed by the claims.

FIG. 1 shows the nucleic acid sequence of rat CTGF clone 2-4-7 and the amino acid sequence encoded by the nucleic acid sequence.

FIG. 2 shows an amino acid sequence comparison of rat (rCTGF) (SEQ ID NO:2), human (Hctgf) (SEQ ID NO:3) and mouse (Mctgf) (SEQ ID NO:4) CTGF polypeptides.

Other objects, features and advantages of the present invention will become apparent from the following detailed description. It should be understood, however, that the detailed description and the specific examples, while indicating preferred embodiments of the invention, are given by way of illustration only, since various changes and modifications within the spirit and scope of the invention will become apparent to those skilled in the art from this detailed description.

DETAILED DESCRIPTION OF THE INVENTION

The present invention discloses the nucleic acid sequence of rat connective tissue growth factor (CTGF) and the protein encoded therefrom. This protein may play a significant role in the normal development, growth and repair of mammalian tissue. The biological activity of CTGF is similar to that of PDGF, however, CTGF is the product of a gene unrelated to the α or β chain genes of PDGF. Since CTGF is produced by endothelial and fibroblastic cells, both of which are present at the site of a wound, it is probable that CTGF functions as a growth factor in wound healing. Pathologically, CTGF may be involved in diseases in which there is an overgrowth of connective tissue cells, such as cancer, fibrotic diseases and atherosclerosis. The CTGF polypeptide could be useful as a therapeutic in cases in which there is impaired healing of skin wounds or there is a need to augment the normal healing mechanisms. Therapeutically, antibodies or fragments of the antibody molecule could also be used to neutralize the biological activity of CTGF in diseases where CTGF is inducing the overgrowth of tissue.

On of the primary biological activity of CTGF polypeptide is its mitogenicity, or ability to stimulate target cells to proliferate. The ultimate result of this mitogenic activity in vivo, is the growth of targeted tissue. A second activity of CTGF polypeptides is related to the role the polypeptide, or fragment thereof, plays in the creation and development of the extracellular matrix, including collagen deposition (ECM). CTGF also possesses chemotactic activity, which is the chemically induced movement of cells as a result of interaction with particular molecules. Preferably, the CTGF of this invention is mitogenic and chemotactic for connective tissue cells, however, other cell types may be responsive to CTGF polypeptide as well.

The term "substantially pure" as used herein refers to CTGFs which are substantially free of other proteins, lipids, carbohydrates or other materials with which they are naturally associated. A substantially pure CTGF polypeptide will yield a single major band on a non-reducing polyacrylamide gel. The purity of CTGFs can also be determined by amino-terminal amino acid sequence analysis. CTGFs, as defined herein, include functional fragments of the polypeptide, so long as CTGF biological activity is retained (e.g., inducing a biologic response in fibroblasts as determined using standard assays common in the art and as taught herein). Smaller polypeptides containing CTGF biological activity are included in the invention. Additionally, more effective CTGFs produced, for example, through site directed mutagenesis of CTGF polypeptide cDNA are included. "Recombinant" CTGFs refer to CTGF polypeptides produced by recombinant DNA techniques; i.e., produced from cells transformed by an exogenous DNA construct encoding the desired CTGF polypeptide. "Synthetic" CTGFs are those prepared by chemical synthesis. A DNA "coding sequence of" or a "nucleotide sequence encoding" a particular CTGF polypeptide, is a DNA sequence which is transcribed and translated into an CTGF polypeptide when placed under the control of appropriate regulatory sequences.

The invention provides polynucleotides encoding the CTGF protein. These polynucleotides include DNA, cDNA and RNA sequences which encode connective tissue growth factor. It is understood that all polynucleotides encoding all or a portion of CTGF are also included herein, so long as they encode a polypeptide with the mitogenic ECM and/or chemotactic activity of CTGF. Such polynucleotides include both naturally occurring and intentionally manipulated polynucleotides. For example, CTGF polynucleotide may be subjected to site-directed mutagenesis. The polynucleotides of the invention include sequences that are degenerate as a result of the genetic code. There are only 20 natural amino acids, most of which are specified by more than one codon. Therefore as long as the amino acid sequence of CTGF is functionally unchanged, all degenerate nucleotide sequences are included in the invention.

Figure 1B:
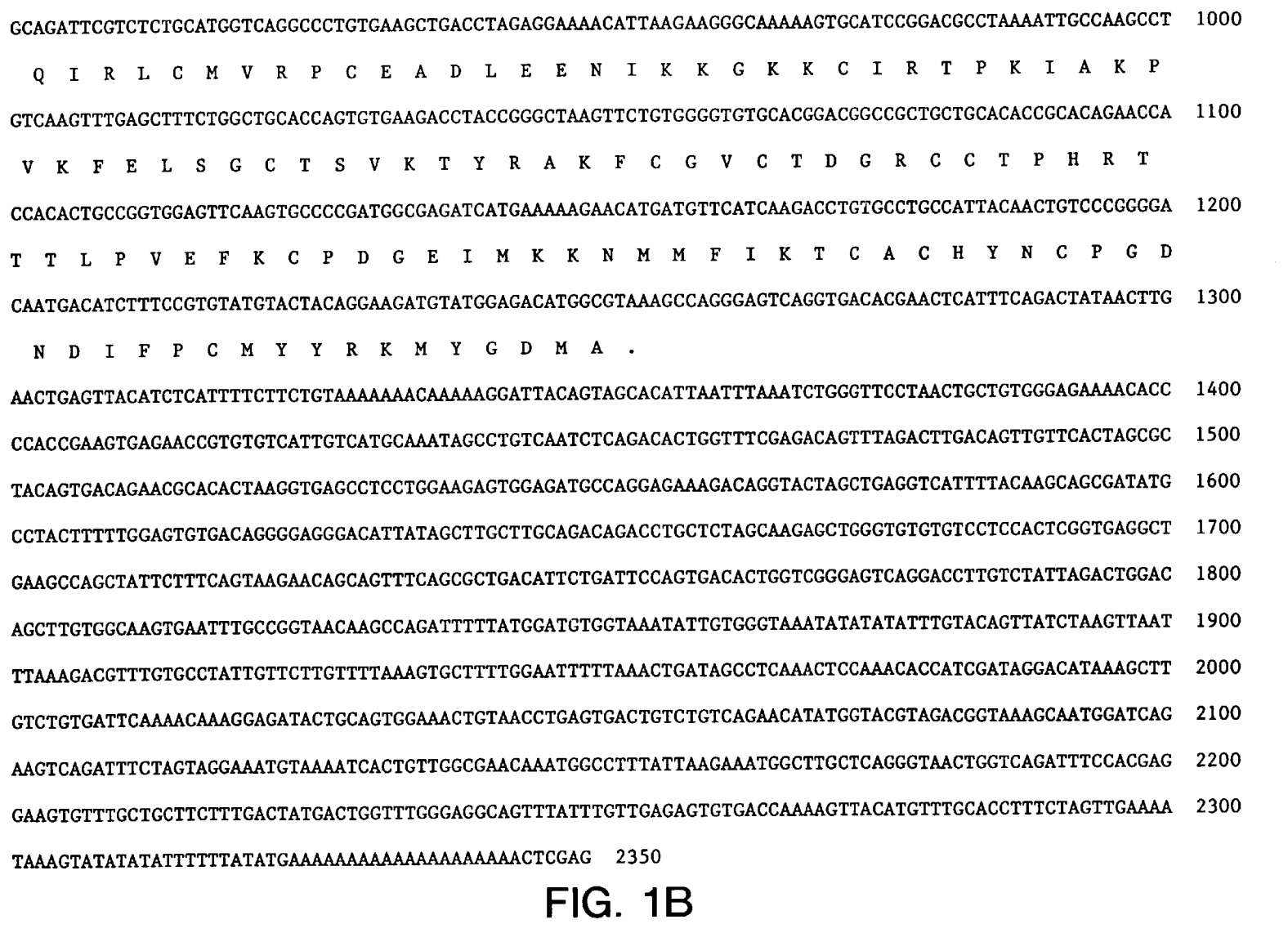

The sequence of the cDNA for rat CTGF (FIG. 1) contains an open reading frame of 2350 nucleotides with an initiation site at position 212 and a TAA termination site at position 1353 and encodes a peptide of 346 amino acids.

By "isolated nucleic acid" is meant a nucleic acid, e.g., a DNA or RNA molecule, that is not immediately contiguous with the 5' and 3' flanking sequences with which it normally is immediately contiguous when present in the naturally occurring genome of the organism from which it is derived. The term thus describes, for example, a nucleic acid that is incorporated into a vector, such as a plasmid or viral vector; a nucleic acid that is incorporated into the genome of a heterologous cell (or the genome of a homologous cell, but at a site different from that at which it naturally occurs); and a nucleic acid that exists as a separate molecule, e.g., a DNA fragment produced by PCR amplification or restriction enzyme digestion, or an RNA molecule produced by in vitro transcription. The term also describes a recombinant nucleic acid that forms part of a hybrid gene encoding additional polypeptide sequences that can be used, for example, in the production of a fusion protein.

The nucleic acid molecules of the invention can be used as templates in standard methods for production of CTGF gene products (e.g., CTGF RNAs and CTGF polypeptides). In addition, the nucleic acid molecules that encode CTGF polypeptides (and fragments thereof) and related nucleic acids, such as (1) nucleic acids containing sequences that are complementary to, or that hybridize to, nucleic acids encoding CTGF polypeptides, or fragments thereof (e.g., fragments containing at least 10, 12, 15, 20, or 25 nucleotides) excluding sequences encoding non-rat CTGF that is already known in the art; and (2) nucleic acids containing sequences that hybridize to sequences that are complementary to nucleic acids encoding CTGF polypeptides, or fragments thereof (e.g, fragments containing at least 10, 12, 15, 20, or 25 nucleotides) excluding sequences encoding non-rat CTGF that is already known in the art; can be used in methods focused on their hybridization properties. For example, as is described in further detail below, such nucleic acid molecules can be used in the following methods: PCR methods for synthesizing CTGF nucleic acids, methods for detecting the presence of an CTGF nucleic acid in a sample, screening methods for identifying nucleic acids encoding new CTGF family members. Oligonucleotide probes useful for screening methods are from 10 to about 150 nucleotides in length. Further, such probes are preferably 10 to about 100 nucleotides in length and more preferably from 10 to about 50 nucleotides in length.

The invention also includes methods for identifying nucleic acid molecules that encode members of the CTGF polypeptide family in addition to SEQ ID NO:1 In these methods, a sample, e.g., a nucleic acid library, such as a rat cDNA library, that contains a nucleic acid encoding a CTGF polypeptide is screened with a CTGF-specific probe, e.g., a CTGF-specific nucleic acid probe. CTGF-specific nucleic acid probes are nucleic acid molecules (e.g., molecules containing DNA or RNA nucleotides, or combinations or modifications thereof) that specifically hybridize to nucleic acids encoding CTGF polypeptides, or to complementary sequences thereof. The term "CTGF-specific probe", in the context of this method of invention, refers to probes that bind to nucleic acids encoding rat CTGF polypeptides, or to complementary sequences thereof, to a detectably greater extent than to nucleic acids encoding other proteins, or to complementary sequences thereof.

The invention facilitates production of CTGF-specific nucleic acid probes. Methods for obtaining such probes can be designed based on the amino acid sequences shown in FIG. 1. The probes, which can contain at least 10, e.g., 15, 25, 35, 50, 100, or 150 nucleotides, can be produced using any of several standard methods (see, e.g., Ausubel, et al., supra). For example, preferably, the probes are generated using PCR amplification methods. In these methods, primers are designed that correspond to CTGF-conserved sequences (see FIG. 1), which can include CTGF-specific amino acids, and the resulting PCR product is used as a probe to screen a nucleic acid library, such as a cDNA library.

Fragments of the full length gene of the present invention may be used as a hybridization probe for a cDNA or a genomic library to isolate the full length DNA and to isolate other DNAs which have a high sequence similarity to the gene or similar biological activity. Probes of this type have at least 10, preferably at least 15, and even more preferably at least 30 bases and may contain, for example, at least 50 or more bases. The probe may also be used to identify a DNA clone corresponding to a full length transcript and a genomic clone or clones that contain the complete gene including regulatory and promotor regions, exons, and introns.

This invention, in addition to the isolated nucleic acid molecule encoding a rat CTGF disclosed in FIG. 1 (SEQ ID NO:1), also provides substantially similar sequences. Isolated nucleic acid sequences are substantially similar if: (i) they are capable of hybridizing under stringent conditions, hereinafter described, to SEQ ID NO:1; or (ii) they encode DNA sequences which are degenerate to SEQ ID NO:1 and such isolated nucleic acid sequences do not encode a known form of CTGF (e.g., human CTGF). Degenerate DNA sequences encode the amino acid sequence of SEQ ID NO:2, but have variations in the nucleotide coding sequences. As used herein, "substantially similar" refers to the sequences having similar identity to the sequences of the instant invention. The nucleotide sequences that are substantially similar can be identified by hybridization or by sequence comparison. Protein sequences that are substantially similar can be identified by one or more of the following: proteolytic digestion, gel electrophoresis and/or microsequencing. One means for isolating a nucleic acid molecule encoding a CTGF protein is to probe a genomic gene library with a natural or artificially designed probe using art recognized procedures (see, for example: Current Protocols in Molecular Biology, Ausubel F. M. et al. (Eds.) Green Publishing Company Assoc. and John Wiley Interscience, New York, 1989, 1992). It is appreciated to one skilled in the art that SEQ ID NO:1, or fragments thereof (comprising at least 10 contiguous nucleotides and at least 70% complementary to a target sequence), is a particularly useful probe. Other particular useful probes for this purpose are hybridizable fragments to the sequences of SEQ ID NO:1 (i.e., comprising at least 10 contiguous nucleotides and at least 70% complementary to a target sequence).

Screening procedures which rely on nucleic acid hybridization make it possible to isolate any gene sequence from any organism, provided the appropriate probe is available. For example, oligonucleotide probes, which correspond to a part of the sequence encoding the protein in question, can be synthesized chemically. This requires that short, oligopeptide stretches of amino acid sequence must be known. The DNA sequence encoding the protein can be deduced from the genetic code, however, the degeneracy of the code must be taken into account. It is possible to perform a mixed addition reaction when the sequence is degenerate. This includes a heterogeneous mixture of denatured double-stranded DNA. For such screening, hybridization is preferably performed on either single-stranded DNA or denatured double-stranded DNA. Hybridization is particularly useful in the detection of cDNA clones derived from sources where an extremely low amount of mRNA sequences relating to the polypeptide of interest is present. In other words, by using selective hybridization conditions directed to avoid non-specific binding, it is possible, for example, to allow the autoradiographic visualization of a specific cDNA clone by the hybridization of the target DNA to that single probe in the mixture which is its complete complement (Wallace, et al., *Nucleic Acid Research,* 9:879, 1981). It is also appreciated that such selective hybridization probes can be and are preferably labeled with an analytically detectable reagent to facilitate identification of the probe. Useful reagents include but are not limited to radioactivity, fluorescent dyes or enzymes capable of catalyzing the formation of a detectable product. The selective hybridization probes are thus useful to isolate complementary copies of DNA from other sources or to screen such sources for related sequences.

With respect to nucleic acid sequences which hybridize to specific nucleic acid sequences disclosed herein, hybridization may be carried out under conditions of reduced stringency, medium stringency or even stringent conditions. As an example of oligonucleotide hybridization, a polymer membrane containing immobilized denatured nucleic acid is first prehybridized for 30 minutes at 45° C. in a solution consisting of 0.9 M NaCl, 50 mM $NaH_2PO_4$, pH 7.0, 5.0 mM $Na_2EDTA$, 0.5% SDS, 10×Denhardt's, and 0.5 mg/mL polyriboadenylic acid. Approximately $2×10^7$ cpm (specific activity of $4×^810$ cpM/$\mu$g)$^{32}$ of P end-labeled oligonucleotide probe are then added to the solution. After 12–16 hours of incubation, the membrane is washed for 30 minutes at room temperature in 1×SET (150 mM NaCl, 20 mM Tris hydrochloride, pH 7.8, 1 mM $Na_2EDTA$) containing 0.5% SDS, followed by a 30 minute wash in fresh 1×SET at Tm-10° C. for the oligo-nucleotide probe. The membrane is then exposed to auto-radiographic film for detection of hybridization signals.

In nucleic acid hybridization reactions, the conditions used to achieve a particular level of stringency will vary, depending on the nature of the nucleic acids being hybridized. For example, the length, degree of complementarity, nucleotide sequence composition (e.g., GC v. AT content), and nucleic acid type (e.g., RNA v. DNA) of the hybridizing regions of the nucleic acids can be considered in selecting hybridization conditions. An additional consideration is whether one of the nucleic acids is immobilized, for example, on a filter.

An example of progressively higher stringency conditions is as follows: 2×SSC/0.1% SDS at about room temperature (hybridization conditions); 0.2×SSC/0.1% SDS at about room temperature (low stringency conditions); 0.2×SSC/ 0.1% SDS at about 42° C. (moderate stringency conditions); and 0.1×SSC at about 68° C. (high stringency conditions). Washing can be carried out using only one of these conditions, e.g., high stringency conditions, or each of the conditions can be used, e.g., for 10–15 minutes each, in the order listed above, repeating any or all of the steps listed. However, as mentioned above, optimal conditions will vary, depending on the particular hybridization reaction involved, and can be determined empirically.

"Selective hybridization" as used herein refers to hybridization under moderately stringent or highly stringent physiological conditions (See, J. Sambrook et al., *Molecular Cloning, A Laboratory Manual,* Cold Spring Harbor Laboratory (Current Edition) which is hereby incorporated by reference in its entirety) that distinguish related from unrelated CTGF based upon the degree of identity between nucleotide sequences in proximity for hybridization to occur. Also, it is understood that a fragment of a 100 bps sequence that is 95 bps in length has 95% identity with the 100 bps sequence from which it is obtained. As used herein, a first DNA (RNA) sequence is at least 70% and preferably at least 80% identical to another DNA (RNA) sequence if there is at least 70% and preferably at least a 80% or 90% identity, respectively, between the bases of the first sequence and the bases of another sequence, when properly aligned with each other, for example, when aligned by BLASTN.

"Identity" as the term is used herein, refers to a polynucleotide sequence which comprises a percentage of the same bases as a reference polynucleotide (SEQ ID NO:1). For example, a polynucleotide which is at least 90% identical to a reference polynucleotide, has polynucleotide bases that are identical in 90% of the bases which make up the reference polynucleotide (i.e., when the sequences are properly aligned with each other using standard alignment and homology adjustments common to those in the art (e.g., NetBlast or GRAIL)) and may have different bases in 10% of the bases which comprise that polynucleotide sequence.

The present invention also relates to polynucleotides which differ from the reference polynucleotide such that the changes are silent changes, for example the changes do not alter the amino acid sequence encoded by the polynucleotide. The present invention also relates to nucleotide changes which result in amino acid substitutions, additions, deletions, fusions and truncations in the protein encoded by the reference polynucleotide (SEQ ID NO:1). In a preferred aspect of the invention these proteins retain the same biological action as the protein encoded by the reference polynucleotide.

It is also appreciated that such probes can be and are preferably labeled with an analytically detectable reagent to facilitate identification of the probe. Useful reagents include but are not limited to radioactivity, fluorescent dyes or proteins capable of catalyzing the formation of a detectable product. The probes are thus useful to isolate complementary copies of DNA from other animal sources or to screen such sources for related sequences.

The invention also includes fragments of rat CTGF polypeptides that retain at least one CTGF-specific activity or epitope. For example, a CTGF polypeptide fragment containing, e.g., at least 8–10 amino acids can be used as an immunogen in the production of CTGF-specific antibodies. The fragment can contain, for example, an amino acid sequence that is conserved in CTGF's. In addition to their use as peptide immunogens, the above-described CTGF fragments can be used in immunoassays, such as ELISAs, to detect the presence of CTGF-specific antibodies in samples.

The CTGF polypeptides of the invention can be obtained using any of several standard methods. For example, CTGF polypeptides can be produced in a standard recombinant expression systems (see below), chemically synthesized (this approach may be limited to small CTGF peptide fragments), or purified from organisms in which they are naturally expressed.

The polynucleotide which encodes the mature protein of FIG. 1 (e.g., SEQ ID NO:1) may include, but is not limited to: only the coding sequence for the mature protein; the coding sequence for the mature protein and additional coding sequence such as a leader sequence or a proprotein sequence; the coding sequence for the mature protein (and optionally additional coding sequence) and non-coding sequence, such as introns or non-coding sequence 5' and/or 3' of the coding sequence for the mature protein.

The fragment, derivative or analog of the protein of FIG. 1 may be (i) one in which one or more of the amino acid residues are substituted with a conserved or non-conserved amino acid residue (preferably a conserved amino acid residue) and such substituted amino acid residue may or may not be one encoded by the genetic code, or (ii) one in which one or more of the amino acid residues includes a substituent group, or (iii) one in which the mature protein is fused with another compound, such as a compound to increase the half-life of the protein (for example, polyethylene glycol), or (iv) one in which the additional amino acids are fused to the mature protein, such as a leader or secretory sequence or a sequence which is employed for purification of the mature protein or a proprotein sequence. Such fragments, derivatives and analogs are deemed to be within the scope of those skilled in the art from the teachings herein.

Thus, the term "polynucleotide encoding a protein" encompasses a polynucleotide which includes only coding sequence for the protein as well as a polynucleotide which includes additional coding and/or non-coding sequence. The isolated nucleic acid sequences and other proteins may then be measured for retention of biological activity characteristic to the protein of the present invention, for example, in an assay for detecting enzymatic CTGF activity. Such proteins include truncated forms of CTGF, and variants such as deletion and insertion variants.

The polynucleotide of the present invention may be in the form of DNA which DNA includes cDNA, genomic DNA, and synthetic DNA. The DNA may be double-stranded or single-stranded, and if single stranded may be the coding strand or non-coding (anti-sense) strand. The coding sequence which encodes the mature protein may be identical to the coding sequences shown in FIGS. 1–6, or may be a different coding sequence which coding sequence, as a result of the redundancy or degeneracy of the genetic code, encodes the same mature protein as the DNA of FIG. 1 (e.g., SEQ ID NO:1).

The present invention further relates to variants of the hereinabove described polynucleotides which encode for fragments, analogs and derivatives of the protein having the deduced amino acid sequence of FIG. 1 (e.g, SEQ ID NO:2). The variant of the polynucleotide may be a naturally occurring allelic variant of the polynucleotide or a non-naturally occurring variant of the polynucleotide.

Thus, the present invention includes polynucleotides encoding the same mature protein as shown in FIG. 1 as well as variants of such polynucleotides which variants encode for a fragment, derivative or analog of the protein of FIG. 1. Such nucleotide variants include deletion variants, substitution variants and addition or insertion variants.

As hereinabove indicated, the polynucleotide may have a coding sequence which is a naturally occurring allelic variant of the coding sequence shown in FIG. 1 (SEQ ID NO:1). As known in the art, an allelic variant is an alternate form of a polynucleotide sequence which may have a substitution, deletion or addition of one or more nucleotides, which does not substantially alter the function of the encoded protein.

The present invention also includes polynucleotides, wherein the coding sequence for the mature protein may be fused in the same reading frame to a polynucleotide sequence which aids in expression and secretion of a protein from a host cell, for example, a leader sequence which functions to control transport of a protein from the cell. The protein having a leader sequence is a preprotein and may have the leader sequence cleaved by the host cell to form the mature form of the protein. The polynucleotides may also encode for a proprotein which is the mature protein plus additional 5' amino acid residues. A mature protein having a prosequence is a proprotein and is an inactive form of the protein. Once the prosequence is cleaved an active mature protein remains.

The present invention further relates to polynucleotides which hybridize to the hereinabove-described sequences if there is at least 70%, preferably at least 90%, and more preferably at least 95% identity between the sequences and wherein the sequences are not previously known in the art. The present invention particularly relates to polynucleotides which hybridize under stringent conditions to the hereinabove-described polynucleotides. As herein used, the term "stringent conditions" means hybridization will occur only if there is at least 95% and preferably at least 97% identity between the sequences. The polynucleotides which hybridize to the hereinabove described polynucleotides in a preferred embodiment encode proteins which either retain substantially the same biological function or activity as the mature protein encoded by the DNA of FIG. 1.

Alternatively, the polynucleotide may have at least 15 bases, preferably at least 30 bases, and more preferably at least 50 bases which hybridize to a polynucleotide of the present invention and which has an identity thereto, as hereinabove described, and which may or may not retain activity. For example, such polynucleotides may be employed as probes for the polynucleotide of SEQ ID NO:1, for example, for recovery of the polynucleotide or as a PCR primer.

Expression of CTGF Polypeptides

DNA sequences encoding CTGF polypeptides can be expressed in vitro by DNA transfer into a suitable host cell. "Host cells" are genetically engineered cells (transduced or transformed or transfected) with the vectors of this invention which may be, for example, a cloning vector or an expression vector. The vector may be, for example, in the form of a plasmid, a viral particle, a phage, etc. The engineered host cells can be cultured in conventional nutrient media modified as appropriate for activating promoters, selecting transformants or amplifying the genes of the present invention. The culture conditions, such as temperature, pH and the like, are those previously used with the host cell selected for expression, and will be apparent to the ordinarily skilled artisan. The term also includes any progeny of the subject host cell. It is understood that all progeny may not be identical to the parental cell since there may be mutations that occur during replication. However, such progeny are included when the term "host cell" is used. Introduction of the construct into the host cell can be effected by calcium phosphate transfection, DEAE-Dextran mediated transfection, electroporation or any other method of the art (Davis, L. et al., *Basic Methods in Molecular Biology*, (Current Edition)).

The nucleic acids of the present invention may be employed for producing CTGFs by recombinant techniques. Thus, for example, the polynucleotide may be included in any one of a variety of expression vectors for expressing CTGF polypeptides. Such vectors include chromosomal, nonchromosomal and synthetic DNA sequences, e.g., derivatives of SV40; bacterial plasmids; phage DNA; baculovirus; yeast plasmids; vectors derived from combinations of plasmids and phage DNA, viral DNA such as vaccinia, adenovirus, fowl pox virus, and pseudorabies. However, any other vector may be used as long as it is replicable and viable in the host.

The appropriate DNA sequence may be inserted into the vector by a variety of procedures. In general, the DNA sequence is inserted into an appropriate restriction endonuclease site(s) by procedures known in the art. Such procedures and others are deemed to be within the scope of those skilled in the art. DNA sequences encoding CTGFs can be expressed in vivo in either prokaryotes or eukaryotes. Methods of expressing DNA sequences having eukaryotic coding sequences in prokaryotes are well known in the art. Hosts include microbial, yeast and mammalian organisms.

DNA sequences encoding CTGF can be expressed in vitro by DNA transfer into a suitable host cell. "Host cells" are cells in which a vector can be propagated and its DNA expressed. The term also includes any progeny of the subject host cell. It is understood that all progeny may not be identical to the parental cell since there may be mutations that occur during replication. However, such progeny are included when the term "host cell" is used.

DNA sequences encoding CTGF can be expressed in vivo in either prokaryotes or eukaryotes. Methods of expressing DNA sequences having eukaryotic coding sequences in prokaryotes are well known in the art. Hosts include microbial, yeast and mammalian organisms.

A cDNA expression library, such as lambda gt11, can be screened indirectly for CTGF peptides having at least one epitope, using antibodies specific for CTGF or antibodies to PDGF which cross react with CTGF. Such antibodies can be either polyclonally or monoclonally derived and used to detect expression product indicative of the presence of CTGF cDNA.

Biologically functional viral and plasmid DNA vectors capable of expression and replication in a host are known in the art. Such vectors are used to incorporate DNA sequences of the invention. In general, expression vectors containing promotor sequences which facilitate the efficient transcription of the inserted eukaryotic genetic sequence are used in connection with the host. The expression vector typically contains an origin of replication, a promoter, and a terminator, as well as specific genes which are capable of providing phenotypic selection of the transformed cells.

A coding sequence is "operably linked to" another coding sequence when RNA polymerase will transcribe the two coding sequences into a single mRNA, which is then translated into a single polypeptide having amino acids derived from both coding sequences. The coding sequences need not be contiguous to one another so long as the expressed sequences are ultimately processed to produce the desired protein.

A DNA "coding sequence of" or a "nucleotide sequence encoding" a particular protein, is a DNA sequence which is transcribed and translated into a protein when placed under the control of appropriate regulatory sequences. A "promotor sequence" is a DNA regulatory region capable of binding RNA polymerase in a cell and initiating transcription of a downstream (3' direction) coding sequence. The promoter is part of the DNA sequence. This sequence region has a start codon at its 3' terminus. The promoter sequence does include the minimum number of bases where elements necessary to initiate transcription at levels detectable above background. However, after the RNA polymerase binds the sequence and transcription is initiated at the start codon (3' terminus with a promoter), transcription proceeds downstream in the 3' direction. Within the promotor sequence will be found a transcription initiation site (conveniently defined by mapping with nuclease S1) as well as protein binding domains (consensus sequences) responsible for the binding of RNA polymerase.

In addition to expression vectors known in the art such as bacterial, yeast and mammalian expression systems, baculovirus vectors may also be used. One advantage to expression of foreign genes in this invertebrate virus expression vector is that it is capable of expression of high levels of recombinant proteins, which are antigenically and functionally similar to their natural counterparts. Baculovirus vectors and the appropriate insect host cells used in conjunction with the vectors will be known to those skilled in the art. The isolation and purification of host cell expressed polypeptides of the invention may be by any conventional means such as, for example, preparative chromatographic separations and immunological separations such as those involving the use of monoclonal or polyclonal antibody.

Transformation of the host cell with the recombinant DNA may be carried out by conventional techniques well known to those skilled in the art. Where the host is prokaryotic, such as E. coli, competent cells which are capable of DNA uptake can be prepared from cells harvested after exponential growth and subsequently treated by the $CaCl_2$ method using procedures well known in the art. Alternatively, $MgCl_2$ or RbCl could be used.

Where the host used is a eukaryote, various methods of DNA transfer can be used. These include transfection of DNA by calcium phosphate-precipitates, conventional mechanical procedures such as microinjection, insertion of a plasmid encased in liposomes, or the use of virus vectors.

Eukaryotic host cells may also include yeast. For example, DNA can be expressed in yeast by inserting the DNA into appropriate expression vectors and introducing the product into the host cells. Various shuttle vectors for the expression of foreign genes in yeast have been reported (Heinemann, J. et al., *Nature*, 340:205, 1989; Rose, M. et al., *Gene*, 60:237, 1987).

Antibodies to CTGF

The invention provides antibodies which are specifically reactive with CTGF polypeptides or fragments thereof. Although this polypeptide may be cross reactive with antibodies to PDGF or CTGF, not all antibodies to CTGFs will also be reactive with PDGF, and not all antibodies to CTGF will be reactive to CTGFs. Antibody which consists essentially of pooled monoclonal antibodies with different epitopic specificities, as well as distinct monoclonal antibody preparations are provided. Monoclonal antibodies are made from antigen containing fragments of the protein by methods well known in the art (Kohler, et al., *Nature* 256:495, 1975; *Current Protocols in Molecular Biology*, Ausubel, et al., ed., 1989). Polyclonal antibodies to the CTGFs of the invention are also included using methods common to those in the art (see Harlow and Lane, 1988, *Antibodies, A Laboratory Manual*, Cold Spring Harbor Laboratory, New York, Current Edition). Monoclonal antibodies specific for CTGFs can be selected, for example, by screening for hybridoma culture supernatants which react with CTGF polypeptides, but do not react with PDGF. Antibodies generated against CTGFs corresponding to the present invention can be obtained by direct injection of the polypeptides into an animal or by administering the polypeptides to an animal, preferably a nonhuman. The antibody so obtained will then bind the polypeptide itself. In this manner, even a sequence encoding only a fragment of the polypeptides can be used to generate antibodies binding the original polypeptides. Such antibodies can then be used to isolate the polypeptides from cells expressing that polypeptide.

For preparation of monoclonal antibodies, any technique which provides antibodies produced by continuous cell line cultures can be used. Examples include the hybridoma technique (Kohler, et al., *Nature* 256:495, 1975), the trioma technique, the human B-cell hybridoma technique (Kozbor et al., 1983, *Immunology Today* 4:72), and the EBV-hybridoma technique to produce human monoclonal antibodies (Cole, et al., 1985, in *Monoclonal Antibodies and Cancer Therapy*, Alan R. Liss, Inc., pp. 77–96).

Techniques described for the production of single chain antibodies (U.S. Pat. No. 4,946,778) can be adapted to produce single chain antibodies to immunogenic peptide products of this invention. Additionally included within the bounds of the invention, are the production and use for diagnostic and therapeutic applications of both "human" and "humanized" antibodies directed to CTGF polypeptides or fragments thereof. Humanized antibodies are antibodies, or antibody fragments, that have the same binding specificity as a parent antibody (i.e., typically of mouse origin), but which have increased human characteristics. Humanized antibodies may be obtained by chain shuffling, or using phage display technology. For example, a polypeptide comprising a heavy or light chain variable domain of a non-human antibody specific for a CTGF is combined with a repertoire of human complementary (light or heavy) chain variable domains. Hybrid pairings which are specific for the antigen of interest are selected. Human chains from the selected pairings may then be combined with a repertoire of human complementary variable domains (heavy or light) and humanized antibody polypeptide dimers can then be selected for binding specificity for an antigen. Such techniques are described in U.S. Pat. No. 5,565,332 or can be obtained commercially (Scotgene, Scotland or Oxford Molecular, Palo Alto, Calif., USA). Furthermore, techniques described for the production of "human" antibodies (i.e., de novo antibodies with human constant region sequences) in transgenic mice (U.S. Pat. Nos. 5,545,806 and 5,569,825) can also be adapted to produce "human" CTGF antibodies or antibody fragments or may also be commercially contracted (GenPharm International, Inc., Mountain View, Calif., USA).

Antibodies generated against the polypeptides of the present invention may be used in screening for similar CTGF polypeptides from other organisms and samples. Such screening techniques are known in the art.

Methods of Treatment

The invention also discloses a method for ameliorating diseases characterized by a cell proliferative disorder by treating the site of the disease with an effective amount of a CTGF reactive agent. The term "ameliorate" denotes a lessening of the detrimental effect of the disease-inducing response in the patient receiving therapy. Where the disease is due to an overgrowth of cells, an antagonist of CTGF polypeptide is effective in decreasing the amount of growth factor that can bind to a CTGF specific receptor on a cell. Such an antagonist may be a CTGF specific antibody or functional fragments thereof (e.g., Fab, F(ab')$_2$). The treatment requires contacting the site of the disease with the antagonist. Where the cell proliferative disorder is due to a diminished amount of growth of cells, a CTGF reactive agent which is stimulatory is contacted with the site of the disease. For example, TGF-$\beta$ is one such reactive agent. Other agents will be known to those skilled in the art.

The terms "treating", "treatment", and the like are used herein to mean obtaining a desired pharmacologic and/or physiologic effect. The effect may be prophylactic in terms of completely or partially preventing a disorder or sign or symptom thereof, and/or may be therapeutic in terms of a partial or complete cure for a disorder and/or adverse effect attributable to the disorder. "Treating" as used herein covers any treatment of a disorder in a mammal, and includes:

(a) preventing a disorder from occurring in a subject that may be predisposed to a disorder, but has not yet been diagnosed as having it;

(b) inhibiting a disorder, i.e., arresting its development; or (c) relieving or ameliorating the disorder, e.g., cause regression of the disorder.

The term "cell proliferative disorder" refers to a condition characterized by an abnormal number of cells. The condition can include both hypertrophic (the continual multiplication of cells resulting in an overgrowth of a cell population within a tissue) and hypotrophic (a lack or deficiency of cells within a tissue) cell growth or an excessive influx or migration of cells into an area of a body. The cell populations are not necessarily transformed, tumorigenic or malignant cells, but can include normal cells as well. For example, CTGFs may be involved in a pathological condition by inducing a proliferative lesion in the intimal layer of an arterial wall, resulting in atherosclerosis. Instead of trying to reduce risk factors for the condition, e.g., lowering blood pressure or reducing elevated cholesterol levels, CTGF polypeptide inhibitors or antagonists of the invention would be useful in interfering with the in vivo activity of CTGFs associated with atherosclerosis. CTGF polypeptide antagonists are also useful in treating other disorders associated with an overgrowth of connective tissues, such as various fibrotic conditions, including scleroderma, arthritis and liver cirrhosis.

These diseases, disorders or ailments modulated by CTGF include tissue repair subsequent to traumatic injuries or conditions including arthritis, osteoporosis and other skeletal disorders, and burn. Because these problems are due to a poor growth response of the fibroblasts, stem cells, chondrocytes, osteoblasts or fibroblasts at the site of injury, the addition of an active biologic agent that stimulates or induces growth of these cells is beneficial. The term "induce" or "induction" as used herein, refers to the activation, stimulation, enhancement, initiation and or maintenance of the cellular mechanisms or processes necessary for the formation of any of the tissue, repair process or development as described herein.

The term "modulate" as used herein, denotes a modification of an existing condition or biologic state. Modulation of a condition as defined herein, encompasses both an increase or a decrease in the determinants affecting the existing condition. For example, administration of CTGFs could be used to augment.

The invention also discloses a method for treating conditions characterized by a cell proliferative disorder by treating the condition using an therapeutically effective amount of a CTGF reactive agent. The term "treat" denotes a lessening of the detrimental effect of the condition in the subject receiving the reactive agent. Where the condition is due to an overgrowth of cells, an antagonist of CTGF is therapeutically effective in decreasing the amount of growth factor that can bind to an CTGF specific receptor on a cell. Such an antagonist may be a CTGF specific antibody or functional fragments thereof (e.g., Fab, F(ab)$_2$). The treatment requires contacting or delivering to the site of the condition with the antagonist of the CTGF polypeptide. Where the cell proliferative disorder is due to a diminished amount of growth of cells, a CTGF reactive agent which is stimulatory is contacted with, or delivered to the site of the condition. For example, TGP-$\beta$ (or another member of the TGP-$\beta$ superfamily) can be such a reactive agent. Other biologic agents will be known to those skilled in the art.

The therapeutic agents useful in the method of the invention can be administered parenterally by injection or by gradual perfusion over time. Administration may be intravenously, intraperitoneally, intramuscularly, subcutaneously, intracavity, or transdermally.

Preparations for parenteral administration include sterile aqueous or non-aqueous solutions, suspensions, and emulsions. Examples of non-aqueous solvents are propylene glycol, polyethylene glycol, vegetable oils such as olive oil, and injectable organic esters such as ethyl oleate. Aqueous carriers include water, alcoholic/aqueous solutions, emulsions or suspensions, including saline and buffered media. Parenteral vehicles include sodium chloride solution, Ringer's dextrose, dextrose and sodium chloride, lactated Ringer's intravenous vehicles include fluid and nutrient replenishers, electrolyte replenishers (such as those based on Ringer's dextrose), and the like. Preservatives and other additives may also be present such as, for example, antimicrobials, anti-oxidants, chelating agents and inert gases and the like.

Another therapeutic approach included within the invention involves direct administration of reagents or compositions including the CTGFs of the invention by any conventional administration technique (for example, but not restricted to, local injection, inhalation, or systemic administration), to a subject with a fibrotic, a scelortic, or a cell proliferative disorder, atherosclerosis. Administration of CTGFs, as described above, accelerate wound healing, can induce the formation of tissue repair or regeneration, or the growth and development of the endometrium. The reagent, formulation or composition may also be targeted to specific cells or receptors by any method described herein or by any method known in the art of delivering, targeting and expressing genes encoding CTGF. The actual dosage of reagent, formulation or composition that modulates a fibrotic disorder, a scelortic disorder, a cell proliferative disorder, atherosclerosis or wound healing depends on many factors, including the size and health of an organism. However, one of ordinary skill in the art can use the following teachings describing the methods and techniques for determining clinical dosages (Spilker B., *Guide to Clinical Studies and Developing Protocols,* Raven Press Books, Ltd., New York, 1984, pp. 7–13, 54–60; Spilker B., *Guide to Clinical Trials,* Raven Press, Ltd., New York, 1991, pp. 93–101; Craig C., and R. Stitzel, eds., *Modern Pharmacology,* 2d ed., Little, Brown and Co., Boston, 1986, pp. 127–33; T. Speight, ed., *Avery's Drug Treatment: Principles and Practice of Clinical Pharmacology and Therapeutics,* 3d ed., Williams and Wilkins, Baltimore, 1987, pp. 50–56; R. Tallarida, R. Raffa and P. McGonigle, *Principles in General Pharmacology,* Springer-Verlag, New York, 1988, pp. 18–20) or to determine the appropriate dosage to use; but, generally, in the range of about between 0.5 µg/ml and 500 µg/ml inclusive final concentration are administered per day to an adult in any pharmaceutically-acceptable carrier.

Polynucleotides for Therapeutic Use

In another embodiment, a method for inhibiting CTGF expression in a subject comprising administering a therapeutically effective amount of a polynucleotide which inhibits such expression. The term "subject" means any mammal, preferably a human. Thus, when a cell proliferative disorder is associated with the expression of CTGFs, a therapeutic approach which directly interferes with the transcription of CTGF into RNA or the translation of CTGF mRNA into protein is possible. A "CTGF target nucleic acid sequence", as used herein, encompasses any nucleic acid encoding a CTGF protein, or fragment thereof. For example, antisense nucleic acid or ribozymes that bind to the CTGF transcript RNA or cleave it are also included within the invention. Antisense RNA or DNA molecules bind specifically with a targeted gene's RNA message, interrupting the expression of that gene's protein product. The antisense binds to the transcript RNA forming a double stranded molecule which cannot be translated by the cell. Antisense oligonucleotides of about 15–25 nucleotides are preferred since they are easily synthesized and have an inhibitory effect just like antisense RNA molecules. In addition, chemically reactive groups, such as iron-linked ethylenediaminetetraacetic acid (EDTA-$F_c$) can be attached to an antisense oligonucleotide, causing cleavage of the RNA at the site of hybridization. These and other uses of antisense methods to inhibit the in vivo translation of genes are well known in the art (e.g., De Mesmaeker, et al., 1995. Backbone modifications in oligonucleotides and peptide nucleic acid systems. *Curr. Opin. Struct. Biol.* 5:343–355; Gewirtz, A. M., et al., 1996b. Facilitating delivery of antisense oligodeoxynucleotides: Helping antisense deliver on its promise; *Proc. Natl. Acad. Sci. U.S.A.* 93:3161–3163; Stein, C. A. A discussion of G-tetrads 1996. Exploiting the potential of antisense: beyond phosphorothioate oligodeoxynucleotides. *Chem. and Biol.* 3:319–323).

"Transcript RNA", as used herein, is RNA which contains nucleotide sequence encoding a protein product. Preferably, the transcript RNA is messenger RNA (mRNA). "mRNA", as used herein, is a single-stranded RNA molecule that specifies the amino acid sequence of one or more polypeptide chains. In addition, transcript RNA can be heterogenous nuclear RNA (hnRNA) or masked RNA. "hnRNA", as the term is used herein, represents the primary transcripts of RNA polymerase II and includes precursors of all messenger RNAs from which introns are removed by splicing. hnRNA are extensively processed to give mRNA which is exported to the cytoplasm where protein synthesis occurs. This processing may include the addition of a 5'-linked 7-methyl-guanylate "cap" at the 5' end and a sequence of adenylate groups at the 3' end, the poly A "tail", as well as the removal of any introns and the splicing together of exons. "Masked RNA", as used herein, is any form of mRNA which is present in inactive form. More specifically, masked RNA constitutes a store of maternal information for protein synthesis that is unmasked (derepressed) during the early stages of morphogenesis.

Antisense nucleic acids are DNA or RNA molecules that are complementary to at least a portion of a specific transcript RNA molecule (Weintraub, *Scientific American,* 262:40, 1990). In the cell, the antisense nucleic acids hybridize to the corresponding transcript RNA, forming a double-stranded molecule. For example, the antisense nucleic acids interfere with the translation of the mRNA, since the cell will not translate a mRNA that is double-stranded. Antisense oligomers of about 15 nucleotides are preferred, since they are easily synthesized and are less likely to cause problems than larger molecules. The use of antisense methods to inhibit the in vitro translation of genes is well known in the art (Marcus-Sakura, *Anal.Biochem.,* 172:289, 1988).

Use of an oligonucleotide to stall transcription is known as the triplex strategy since the oligomer winds around double-helical DNA, forming a three-strand helix. Therefore, these triplex compounds can be designed to recognize a unique site on a chosen gene (Maher, et al., *Antisense Res. and Dev.,* 1)(3):227, 1991; Helene, C., *Anticancer Drug Design,* 6(6 :569, 1991).

Ribozymes are RNA molecules possessing the ability to specifically cleave other single-stranded RNA in a manner analogous to DNA restriction endonucleases. Through the modification of nucleotide sequences which encode these RNAs, it is possible to engineer molecules that recognize specific nucleotide sequences in an RNA molecule and cleave it (Cech, *J.Amer.Med. Assn.,* 260:3030, 1988). A major advantage of this approach is that, because they are sequence-specific, only mRNAs with particular sequences are inactivated.

There are two basic types of ribozymes namely, tetrahymena-type (Hasselhoff, *Nature*, 334:585, 1988) and "hammerhead"-type. Tetrahymena-type ribozymes recognize sequences which are four bases in length, while "hamnmerhead"-type ribozymes recognize base sequences 11–18 bases in length. The longer the recognition sequence, the greater the likelihood that the sequence will occur exclusively in the target mRNA species. Consequently, hammerhead-type ribozymes are preferable to tetrahymena-type ribozymes for inactivating a specific mRNA species and 18-based recognition sequences are preferable to shorter recognition sequences.

These and other uses of antisense methods to inhibit the in vivo translation of genes are well known in the art (e.g., De Mesmaeker, et al., 1995. Backbone modifications in oligonucleotides and peptide nucleic acid systems. *Curr. Opin. Struct. Biol.* 5:343–355; Gewirtz, A. M., et al., 1996b. Facilitating delivery of antisense oligodeoxynucleotides: Helping antisense deliver on its promise; *Proc. Natl. Acad. Sci. U.S.A.* 93:3161–3163; Stein, C. A. A discussion of G-tetrads 1996. Exploiting the potential of antisense: beyond phosphorothioate oligodeoxynucleotides. *Chem. and Biol.* 3:319–323).

The sequence of an antisense polynucleotide useful for inhibiting expression of CTGF can be obtained, for example, by comparing the sequences of orthologous genes, or the transcripts of orthologous genes, and identifying highly conserved regions within the orthologous sequences. Thus, the identification of highly conserved regions contained in nucleic acid sequences encoding rat, human and mouse CTGF can be used to design polynucleotides useful for inhibiting CTGF expression. As used herein, an "orthologous sequence" is that in which sequence homology is retained or conserved between species. Two gene sequences from different organisms are orthologs if they derived from the same gene in the closest ancestor to the two organisms. For example, all vertebrate globin genes are homologous in that their genes are derived from a single globin gene in early vertebrates. Consequently, human and horse a-globin genes, and transcripts encoded therefrom, are orthologous because they have a common ancestor and share significant sequence homology. Therefore, polynucleotides can be designed such that they contain nucleic acid sequence which is, for example, wholly or partially complementary to conserved sequences identified from orthologous sequences.

Similarity in nucleic acid sequences may be determined by procedures and algorithms which are well-known in the art. Such procedures and algorithms include, for example, a BLAST program (Basic Local Alignment Search Tool at the National Center for Biological Information), ALIGN, AMAS (Analysis of Multiply Aligned Sequences), AMPS (Protein Multiple Sequence Alignment), ASSET (Aligned Segment Statistical Evaluation Tool), BANDS, BESTSCOR, BIOSCAN (Biological Sequence Comparative Analysis Node), BLIMPS (BLocks IMProved Searcher), FASTA, Intervals & Points, BMB, CLUSTAL V, CLUSTAL W, CONSENSUS, LCONSENSUS, WCONSENSUS, Smith-Waterman algorithm, DARWIN, Las Vegas algorithm, FNAT (Forced Nucleotide Alignment Tool), Framealign, Framesearch, DYNAMIC, FILTER, FSAP (Fristensky Sequence Analysis Package), GAP (Global Alignment Program), GENAL, GIBBS, GenQuest, ISSC (Sensitive Sequence Comparison), LALIGN (Local Sequence Alignment), LCP (Local Content Program), MACAW (Multiple Alignment Construction & Analysis Workbench), MAP (Multiple Alignment Program), MBLKP, MBLKN, PIMA (Pattern-Induced Multi-sequence Alignment), SAGA (Sequence Alignment by Genetic ALgorithm) and WHAT-IF.

In selecting the preferred length for a given polynucleotide, various factors should be considered to achieve the most favorable characteristics. In one aspect, polynucleotides of the present invention are at least 15 bp in length and preferably about 15 to about 100 bp in length. More preferably, the polynucleotides are about 15 bp to about 80 bp in length and even more preferably, the polynucleotides of the present invention are about 15 to about 60 bp in length. Shorter polynucleotides such as 10-to under 15-mers, while offering higher cell penetration, have lower gene specificity. In contrast, while longer polynucleotides of 20–30 bases offer better specificity, they show decreased uptake kinetics into cells. See Stein et al., "Oligodeoxynucleotides: Antisense Inhibitors of Gene Expression" Cohen, ed. McMillan Press, London (1988). Accessibility to transcript RNA target sequences also is of importance and, therefore, loop-forming regions and orthologous sequences in targeted RNAs offer promising targets. In this disclosure the term "polynucleotide" encompasses both oligomeric nucleic acid moieties of the type found in nature, such as the deoxyribonucleotide and ribonucleotide structures of DNA and RNA, and man-made analogues which are capable of binding to nucleic acids found in nature. The polynucleotides of the present invention can be based upon ribonucleotide or deoxyribonucleotide monomers linked by phosphodiester bonds, or by analogues linked by methyl phosphonate, phosphorothioate, or other bonds. They may also comprise monomer moieties which have altered base structures or other modifications, but which still retain the ability to bind to naturally occurring transcript RNA structures. Such polynucleotides may be prepared by methods well-known in the art, for instance using commercially available machines and reagents such as those available from Perkin-Elmer/Applied Biosystems (Foster City, Calif.). For example, polynucleotides specific to a targeted transcript are synthesized according to standard methodology. Phosphorothioate modified DNA polynucleotides typically are synthesized on automated DNA synthesizers available from a variety of manufacturers. These instruments are capable of synthesizing nanomole amounts of polynucleotides as long as 100 nucleotides. Shorter polynucleotides synthesized by modem instruments are often suitable for use without further purification. If necessary, polynucleotides may be purified by polyacrylamide gel electrophoresis or reverse phase chromatography. See Sambrook et al., *Molecular Cloning: A Laboratory Manual*, Vol. 2, Chapter 11, Cold Spring Harbor Laboratory Press, Cold Spring Harbor, N.Y. (1989).

Phosphodiester-linked polynucleotides are particularly susceptible to the action of nucleases in serum or inside cells, and therefore in a preferred embodiment, the polynucleotides of the present invention are phosphorothioate or methyl phosphonate-linked analogues, which have been shown to be nuclease-resistant. Persons of ordinary skill in this art can easily select other linkages for use in the invention. These modifications also may be designed to improve the cellular uptake and stability of the polynucleotides.

An appropriate carrier for administration of a polynucleotide can include, for example, vectors, antibodies, pharmacologic compositions, binding or homing proteins, or viral delivery systems to enrich for the sequence into the target cell or tissue. A polynucleotide of the present invention can be coupled to, for example, a binding protein which recognizes endothelial cells or tumor cells. Following administration, a polynucleotide of the present invention can be targeted to a recipient cell or tissue such that enhanced expression of, for example, cytokines, transcription factors, G-protein coupled receptors, tumor suppressor proteins and apoptosis initiation proteins can occur.

Delivery of antisense, triplex agents, ribozymes, competitive inhibitors and the like can be achieved using a recombinant expression vector such as a chimeric virus or a colloidal dispersion system. Various viral vectors which can be utilized for gene therapy as taught herein include adenovirus, herpes virus, vaccinia, or, preferably, an RNA virus such as a retrovirus. Preferably, the retroviral vector is a derivative of a murine or avian retrovirus. Examples of retroviral vectors in which a single foreign gene can be inserted include, but are not limited to: Moloney murine leukemia virus (MoMuLV), Harvey murine sarcoma virus (HaMuSV), murine mammary tumor virus (MuMTV), and Rous Sarcoma Virus (RSV). A number of additional retroviral vectors can incorporate multiple genes. All of these vectors can transfer or incorporate a gene for a selectable marker so that transduced cells can be identified and generated. By inserting a polynucleotide sequence of interest into the viral vector, along with another gene which encodes the ligand for a receptor on a specific target cell, for example, the vector is now target specific. Retroviral vectors can be made target specific by inserting, for example, a polynucleotide encoding a sugar, a glycolipid, or a protein. Preferred targeting is accomplished by using an antibody to target the retroviral vector. Those of skill in the art will know of, or can readily ascertain without undue experimentation, specific polynucleotide sequences which can be inserted into the retroviral genome to allow target specific delivery of the retroviral vector containing the antisense polynucleotide.

Since recombinant retroviruses are defective, they require assistance in order to produce infectious vector particles. This assistance can be provided, for example, by using helper cell lines that contain plasmids encoding all of the structural genes of the retrovirus under the control of regulatory sequences within the LTR. These plasmids are missing a nucleotide sequence which enables the packaging mechanism to recognize an RNA transcript for encapsidation. Helper cell lines which have deletions of the packaging signal include but are not limited to $\Psi$2, PA317 and PA12, for example. These cell lines produce empty virions, since no genome is packaged. If a retroviral vector is introduced into such cells in which the packaging signal is intact, but the structural genes are replaced by other genes of interest, the vector can be packaged and vector virion produced.

Alternatively, NIH 3T3 or other tissue culture cells can be directly transfected with plasmids encoding the retroviral structural genes gag, pol and env, by conventional calcium phosphate transfection. These cells are then transfected with the vector plasmid containing the genes of interest. The resulting cells release the retroviral vector into the culture medium.

Another targeted delivery system for antisense polynucleotides a colloidal dispersion system. Colloidal dispersion systems include macromolecule complexes, nanocapsules, microspheres, beads, and lipid-based systems including oil-in-water emulsions, micelles, mixed micelles, and liposomes. The preferred colloidal system of this invention is a liposome. Liposomes are artificial membrane vesicles which are useful as delivery vehicles in vitro and in vivo. It has been shown that large unilamellar vesicles (LUV), which range in size from 0.2–4.0 um can encapsulate a substantial percentage of an aqueous buffer containing large macromolecules. RNA, DNA and intact virions can be encapsulated within the aqueous interior and be delivered to cells in a biologically active form (Fraley, et al., *Trends Biochem. Sci.*, 6:77, 1981). In addition to mammalian cells, liposomes have been used for delivery of polynucleotides in plant, yeast and bacterial cells. In order for a liposome to be an efficient gene transfer vehicle, the following characteristics should be present: (1) encapsulation of the genes of interest at high efficiency while not compromising their biological activity; (2) preferential and substantial binding to a target cell in comparison to non-target cells; (3) delivery of the aqueous contents of the vesicle to the target cell cytoplasm at high efficiency; and (4) accurate and effective expression of genetic information (Mannino, et al., *Biotechniques*, 6:682, 1988).

The term "effective amount" or "therapeutically effective amount", as used herein, is the amount sufficient to obtain the desired physiological effect, e.g., treatment of a disorder. An effective amount of the vector expressing, for example, a polynucleotide of the invention is generally determined by the physician in each case on the basis of factors normally considered by one skilled in the art to determine appropriate dosages, including the age, sex, and weight of the subject to be treated, the condition being treated, and the severity of the medical condition being treated.

Administration of a polynucleotide to a subject, either as a naked, synthetic polynucleotide or as part of an expression vector, can be effected via any common route (oral, nasal, buccal, rectal, vaginal, or topical), or by subcutaneous, intramuscular, intraperitoneal, or intravenous injection. Pharmaceutical compositions of the present invention, however, are advantageously administered in the form of injectable compositions. A typical composition for such purpose comprises a pharmaceutically acceptable solvent or diluent and other suitable, physiologic compounds. For instance, the composition may contain polynucleotides and about 10 mg of human serum albumin per milliliter of a phosphate buffer containing NaCl. As much as 700 milligrams of a polynucleotide has been administered intravenously to a patient over a course of 10 days (i.e., 0.05 mg/kg/hour) without signs of toxicity. Sterling, "Systemic Antisense Treatment Reported," *Genetic Engineering News* 12:1, 28 (1992).

The composition of the liposome is usually a combination of phospholipids, particularly high-phase-transition-temperature phospholipids, usually in combination with steroids, especially cholesterol. Other phospholipids or other lipids may also be used. The physical characteristics of liposomes depend on pH, ionic strength, and the presence of divalent cations.

Examples of lipids useful in liposome production include phosphatidyl compounds, such as phosphatidylglycerol, phosphatidylcholine, phosphatidylserine, phosphatidylethanolamine, sphingolipids, cerebrosides, and gangliosides. Particularly useful are diacylphosphatidylglycerols, where the lipid moiety contains from 14–18 carbon atoms, particularly from 16–18 carbon atoms, and is saturated. Illustrative phospholipids include egg phosphatidylcholine, dipalmitoylphosphatidylcholine and distearoylphosphatidylcholine.

The targeting of liposomes has been classified based on anatomical and mechanistic factors. Anatomical classification is based on the level of selectivity, for example, organ-specific, cell-specific, and organelle-specific. Mechanistic targeting can be distinguished based upon whether it is passive or active. Passive targeting utilizes the natural tendency of liposomes to distribute to cells of the reticuloendothelial system (RES) in organs which contain sinusoidal capillaries. Active targeting, on the other hand, involves alteration of the liposome by coupling the liposome to a specific ligand such as a monoclonal antibody, sugar, glycolipid, or protein, or by changing the composition or size of the liposome in order to achieve targeting to organs and cell types other than the naturally occurring sites of localization.

The surface of the targeted delivery system may be modified in a variety of ways. In the case of a liposomal targeted delivery system, lipid groups can be incorporated into the lipid bilayer of the liposome in order to maintain the targeting ligand in stable association with the liposomal bilayer. Various linking groups can be used for joining the lipid chains to the targeting ligand. In general, the compounds bound to the surface of the targeted delivery system will be ligands and receptors which will allow the targeted delivery system to find and "home in" on the desired cells. A ligand may be any compound of interest which will bind to another compound, such as a receptor.

The following examples are put forth so as to provide those of ordinary skill in the art with a complete disclosure and description of how to make and use the CTGFs of the present invention, and are not intended, nor should they be construed, to limit the scope of what the inventors regard as their invention. Efforts have been made to ensure accuracy with respect to numbers used (e.g, amounts, time, temperature, etc.) but some experimental errors and deviations should be accounted for. Unless indicated otherwise, parts are parts by weight, molecular weight is weight average molecular weight, temperature is in degrees Centigrade, and pressure is at or near atmospheric.

EXAMPLE 1

The strategy was to clone rat CTGF clone by polymerase chain reaction (PCR) Four oligonucleotides, two sense (F1 and F2) and two anti-sense (R1 and R2), were designed based on homologous regions between mouse and human CTGF. The sequence of the F2 oligonucleotide is 5'-GAGTGGGTGTGTGACGAGCCCAAGG-3' (SEQ ID NO:5). The sequence of the R1 oligonucleotide is 5'-ATGTCTCCGTACATCTTCCTGTAGT-3' (SEQ ID NO:6). PCR was performed using combination of these oligonucleotides to amplify a region of the rat CTGF from an NRK library (normal rate kidney fibroblast). The PCR products were analyzed and products from the primer combinations F2/R1 and F2/R2 were cloned into pCR vector (InVitrogen) according to instructions. Two clones from F2/R1 reaction were sequenced and showed homology to human CTGF and fisp 12. The full length cDNA was cloned from the original NRK library by limited dilution. Plate lysates were made from a 1/50,000 dilution of the NRK library. Two of these plate lysates were F2/R1 PCR positive, #2 and #4. These lysates were plated and ten pools of ten plaques were picked and screened by F2/R1 PCR. Two pools from lysate #2 were positive, #2 and #4. Pools 2—2 and 2-1 were plated and single plaques picked and screened by F2/R1 PCR. The single plaque 2-4-7 was PCR positive and was converted into a plasmid according to the manufacture's instructions (Statagene). The DNA was prepared and sequenced, FIG. 1. The sequence of clone 2-4-7 is homologous to human CTGF and mouse CTGF (fisp 12), FIG. 2.

It will be apparent to those skilled in the art that various modifications and variations can be made to the compounds and processes of this invention. Thus, it is intended that the present invention cover such modifications and variations, provided they come within the scope of the appended claims and their equivalents. Accordingly, the invention is limited only by the following claims.

What is claimed is:

1. An isolated polynucleotide sequence encoding a polypeptide having an amino acid sequence as set forth in SEQ ID NO:2.

2. An isolated polynucleotide selected from the group consisting of:
   a) SEQ ID NO:1;
   b) SEQ ID NO:1, wherein T can also be U;
   c) nucleic acid sequences complementary to a) or b); and
   d) degenerate sequences of a), b) or c).

3. An expression vector including a polynucleotide of claim 2.

4. The vector of claim 3, wherein the vector is a plasmid.

5. The vector of claim 3, wherein the vector is a virus-derived.

6. A host cell stably transformed with the vector of claim 3.

7. The host cell of claim 6, wherein the cell is prokaryotic.

8. The host cell of claim 6, wherein the cell is eukaryotic.

9. A method for producing a Connective Tissue Growth Factor polypeptide comprising:
   a) culturing a host cell of claim 6,
   b) expressing from the host cell of claim 6, a polypeptide encoded by said DNA; and
   c) isolating the polypeptide.

* * * * *